(12) United States Patent
Turdjian

(10) Patent No.: US 8,671,948 B2
(45) Date of Patent: Mar. 18, 2014

(54) CORDED EARPLUGS

(75) Inventor: Crest Turdjian, Los Angeles, CA (US)

(73) Assignee: Moldex-Metric, Inc., Culver City, CA (US)

( * ) Notice: Subject to any disclaimer, the term of this patent is extended or adjusted under 35 U.S.C. 154(b) by 147 days.

(21) Appl. No.: 12/924,462

(22) Filed: Sep. 28, 2010

(65) Prior Publication Data

US 2012/0073583 A1    Mar. 29, 2012

(51) Int. Cl.
*A61F 11/00* (2006.01)
*A61F 11/06* (2006.01)
*A61B 7/02* (2006.01)

(52) U.S. Cl.
USPC ............................ 128/864; 128/867; 181/867

(58) Field of Classification Search
USPC .......... 128/864, 865, 866, 867–868; 181/129, 181/130, 134, 135, 294; D24/106, 174; D29/112; 381/312, 317, 322, 324
See application file for complete search history.

(56) References Cited

U.S. PATENT DOCUMENTS 4,253,452 A * 3/1981 Powers et al. ................. 128/864
5,711,313 A * 1/1998 Fleming ......................... 128/864

* cited by examiner

*Primary Examiner* — Patricia Bianco
*Assistant Examiner* — Ophelia A Hawthorne
(74) *Attorney, Agent, or Firm* — Charles H. Schwartz

(57) ABSTRACT

An apparatus and a method of making a corded earplug, including a flexible cord material and a pair of earplugs. Each earplug has a nose portion for insertion into the ear and a rear portion extending from the nose portion and lying outside of the ear when the nose portion is inserted into the ear. Each rear portion has a pair of openings physically displaced from each other and/or angularly displaced from each other. At least one of the openings extends through the rear portion. A short portion of the flexible cord material is inserted through the at least one opening extending through the rear portion. The short portion of the flexible cord material is then inserted into the other opening to have the short portion of the flexible cord material physically displaced and/or angularly displaced along its length to lock the flexible cord material to the rear portion of the earplug.

12 Claims, 1 Drawing Sheet

CORDED EARPLUGS

BACKGROUND OF THE INVENTION

The present invention relates to a corded earplug and additionally to a method for making such a corded earplug.

In the prior art, corded earplugs are generally made by initially making an earplug by any conventional technique. The earplugs are either produced with an elongated opening at one end or an elongated opening is made at one end of the earplug after it has been produced. An adhesive is then applied to the opening and one end of a cord is inserted into the elongated opening during the short time that the adhesive is liquid. This adhesive then bonds the cord within the opening at one end of the earplug and generally a pair of such earplugs are located at opposite ends of the cord. This produces the conventional type of corded earplug, which includes a number of additional steps after the earplugs are produced.

The difficulty with prior art corded earplugs is that it is difficult to insert the cord into the opening during the short period of time that the adhesive is liquid. In addition this method of attaching the cord to the earplug can result in a bond that is completely dependent on the adhesive and therefore may not be very strong. Also, this method is permanent and does not allow for the pair of earplugs to be used without a cord. Other prior art corded earplugs use a cord with ends that can be inserted into an opening in the earplugs but are easily removable if desired so that the earplugs can be used without the cord. Since the attachment of the cord to the earplugs is easily removable, the earplugs can be disengaged from the cord when this is not desired.

It would therefore be desirable to provide for a method of attaching a cord to an earplug using a method and apparatus that is simpler than the prior art and also produces strong connection between the cord and the earplug.

SUMMARY OF THE PRESENT INVENTION

The present invention is directed to a corded earplug, and specifically to a method of making a corded earplug including providing a flexible cord material and a pair of earplugs. Each earplug has a nose portion for insertion into the ear and a rear portion extending from the nose portion and lying outside of the ear. Each rear portion of each earplug has a pair of openings physically displaced from each other and/or angularly displaced from each other. At least a first one of the openings extends completely through the rear portion. A short portion of the flexible cord material is inserted through the at least first one opening and then the short portion is inserted into the second other opening to have the short portion of the flexible cord material physically displaced and/or angularly displaced along its length to lock the flexible cord material to the rear portion of the earplug.

Because of this technique, the cord itself loops around to produce a very strong attachment to the rear of the earplugs. However, if desired, the technique can be reversed by first removing the end of the cord from the second opening and then pulled through the first opening to detach the cord from the earplug.

The present invention can be used with any type of earplug, such as a molded foam type with a plastic insert or handle or an earplug made out of a resilient elastomeric rubber-like material. The cord itself can be made of a braided material similar to a shoelace or from an elastomeric rubber-like material.

DETAILED DESCRIPTION OF THE DRAWINGS

Figure 1:
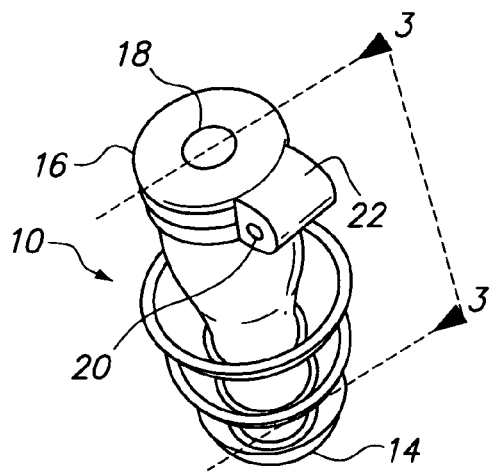
FIG. 1 illustrates a perspective view of an earplug that can be removable attached to a cord or used without a cord.
Figure 2:
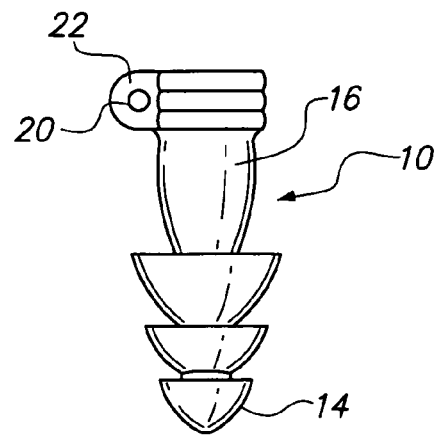
FIG. 2 illustrates a side view of the earplug of FIG. 1.
Figure 4:
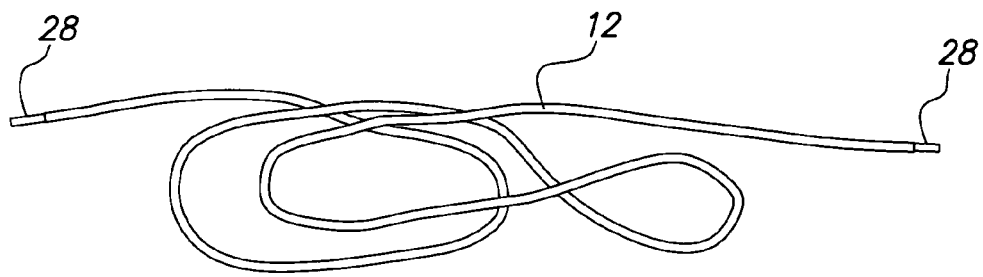
FIG. 4 illustrates a cord for producing a corded earplug using a pair of earplugs of FIG. 1.
Figure 3:
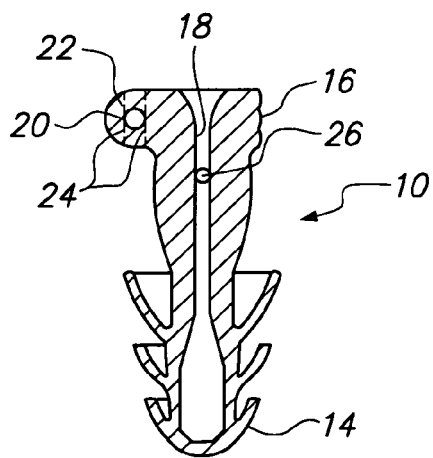
FIG. 3 illustrates a side cross-sectional view of the earplug of FIG. 1 taken along lines 3-3 of FIG. 1.

As in FIGS. 1-3, an earplug 10 is shown and wherein a pair of earplugs 10 may be located at the ends of a flexible cord 12 shown in FIG. 4. The present invention can be incorporated with any type of earplug, such as a molded foam type with a plastic insert or handle or an earplug made out of a resilient elastomeric rubber-like material. The earplug may be a flanged type earplug such as shown in FIGS. 1-3 or may be an un-flanged type of earplug.

In general, all earplugs have a nose portion 14 and a rear portion 16. The nose portion 14 is for insertion into the ear and the rear portion 16 extends from the nose portion and lies outside of the ear. In the present invention, the rear portion 16 also includes a pair of openings 18 and 20 that are physically displaced from each other and angularly displaced from each other. The opening 18 extends in a vertical direction into the earplug 10 and the opening 20 extends in a horizontal direction completely through a flange portion 22 projecting from the rear portion 14 of the earplug 10.

In the example shown in FIGS. 1-3, the openings are angularly displaced 90 degrees from each other but it will be appreciated that the angular relationship can be zero degrees to one hundred eighty degrees as long as there is a physical displacement that produces a looping of the cord during attachment of the cord 12 to the rear portion of the earplug 10. As one example, the flange 22 can have the opening 20 can pass through the flange 22 in a vertical direction. This can be seen in FIG. 3 by the dotted lines 24 that represent an opening passing through the flange 22 in a vertical direction so there is no angular displacement.

Concurrently, the physical displacement can be zero as long as the angular displacement produces a looping of the cord during attachment of the cord 12 to the rear portion of the earplug 10. As one example, the flange 22 can be eliminated and the opening 20 can pass through the rear portion 16. This can be seen in FIG. 3 by the dotted circular line 26 that represent an opening passing through the rear portion 16 in a horizontal direction so there is no physical displacement.

The cord 12 may be formed of a smooth plastic or may be formed of some cloth-like woven or braided material. In any event the use of the cord 12 to support the earplugs 10 is a useful feature. The earplugs can be inserted into the ear and then removed and with the cord draped around the neck to keep the earplugs located with user without having to store the earplugs in some other place. The cord 12 has end portions 28 that are more rigid than the remaining length of the cord. The ends can be similar to the ends of an ordinary shoelace and can be manufactured in any conventional way such as using a plastic sleeve to enclose the end portions 28 or dipping the ends into a plastic material that hardens to make the end portions 28 more rigid.

Figure 5:
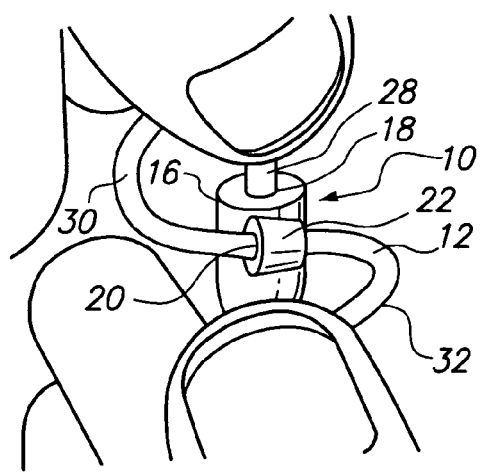
FIG. 5 illustrates the technique of attaching the cord of FIG. 4 to the earplug of FIG. 1.

FIG. 5 illustrates the method of attaching the cord 12 to the rear portion 16 of the earplug 10. As shown, the end portion 28 of the cord 12 is first passed through the opening 20 in the flange 22 and then looped up to be inserted into the opening 18 in the rear portion 16 of the earplug 10 to form a loop portion 30 of the cord 10. The end of the cord 12 is now firmly attached to the rear portion 16 of the earplug 10 and if a pulling force is applied to an outside portion 32 of the cord 12 shown in FIG. 5, all the pulling force will do is tighten and shorten the loop portion 30 of the cord 12 to the rear portion 16 of the earplug 10. To remove the cord 12 from the rear portion 16 of the earplug 10 the above steps are reversed. The end portion 28 of the cord 12 is removed from the opening 18 and the cord 12 is then pulled through the opening 20.

The present invention produces a corded earplug where the cord is securely attached to the ends of the earplugs. This attachment method and structure is simple and eliminates the difficulties of the prior art of applying an adhesive and then inserting the cord into the end of an earplug during the short time that the adhesive is liquid. The method shown in the present invention provides for an extremely strong attachment between the cord and the end of the earplug yet allowing the removal of the cord if desired.

Although the invention has been described with reference to particular embodiments, it should be appreciated that various adaptations and modifications may be made and the invention is only to be limited by the appended claims.

I claim:

1. A method of making a corded earplug, including the following steps:
   providing a flexible cord material,
   providing a pair of earplugs and with each earplug having a nose portion for insertion into the ear and a rear portion extending from the nose portion and lying outside of the ear when the nose portion is inserted into the ear,
   providing each rear portion with a pair of openings physically displaced from each other or angularly displaced from each other and with at least one opening extending through the rear portion,
   inserting a short portion of the flexible cord material through the at least one opening extending through the rear portion, and
   inserting the short portion of the flexible cord material after the short portion of the flexible cord material has been extended through the at least one opening extending through the rear portion into the other opening in the rear portion to have the short portion of the flexible cord material physically displaced or angularly displaced along its length to lock the flexible cord material to the rear portion of the earplug.

2. The method of claim 1 wherein the pair of openings are physically displaced from each other and angularly displaced from each other and the angular displacement is 90 degrees.

3. The method of claim 1 wherein the at least one opening extending through the rear portion is provided in a section of the rear portion that extends outwardly.

4. The method of claim 1 wherein the at least one opening extending through the rear portion is provided in a section of the rear portion that extends outwardly and the at least one opening is horizontal relative to the other opening that is vertical.

5. A corded earplug, including the following:
   a flexible cord material,
   a pair of earplugs and with each earplug having a nose portion for insertion into the ear and a rear portion extending from the nose portion and lying outside of the ear when the nose portion is inserted into the ear,
   each rear portion having a pair of openings physically displaced from each other or angularly displaced from each other and with at least one opening extending through the rear portion,
   a short portion of the flexible cord material for inserting through the at least one opening extending through the rear portion, and
   the short portion of the flexible cord material after the short portion of the flexible cord material has been inserted through the at least one opening extending through the rear portion inserted into the other opening in the rear portion to have the short portion of the flexible cord material physically displaced or angularly displaced along its length to lock the flexible cord material to the rear portion of the earplug.

6. The corded earplug of claim 5 wherein the pair of openings are physically displaced from each other and angularly displaced from each other and the angular displacement is 90 degrees.

7. The corded earplug of claim 5 wherein the at least one opening extending through the rear portion is provided in a section of the rear portion that extends outwardly.

8. The corded earplug of claim 5 wherein the at least one opening extending through the rear portion is provided in a section of the rear portion that extends outwardly and the at least one opening is horizontal relative to the other opening that is vertical.

9. A pair of earplugs attached to opposite ends of a flexible cord, including the following,
   a pair of earplugs and with each earplug having a nose portion for insertion into the ear and a rear portion extending from the nose portion and lying outside of the ear when the nose portion is inserted into the ear,
   each rear portion having a pair of openings physically displaced from each other or angularly displaced from each other and with at least one opening extending through the rear portion, and
   wherein the pair of earplugs is attached to the opposite ends of the flexible cord using a short portion of the flexible cord at each end by inserting each short portion through the at least one opening extending through the rear portion and then inserting the short portion into the other opening in the rear portion to have the short portion of the flexible cord material physically displaced or angularly displaced along its length to lock the flexible cord material to the rear portion of the earplug.

10. The pair of earplugs of claim 9 wherein the pair of openings are physically displaced from each other and angularly displaced from each other and the angular displacement is 90 degrees.

11. The pair of earplugs of claim 9 wherein the at least one opening extending through the rear portion is provided in a section of the rear portion that extends outwardly.

12. The pair of earplugs of claim 9 wherein the at least one opening extending through the rear portion is provided in a section of the rear portion that extends outwardly and the at least one opening is horizontal relative to the other opening that is vertical.

* * * * *